United States Patent
Nekelson et al.

(10) Patent No.: US 11,355,715 B2
(45) Date of Patent: Jun. 7, 2022

(54) SUBSTITUTED BENZONAPHTHATHIOPHENE COMPOUNDS FOR ORGANIC ELECTRONICS

(71) Applicant: Clap Co., Ltd., Seoul (KR)

(72) Inventors: Fabien Nekelson, Amagasaki (JP); Fulvio Giacomo Brunetti, Ludwigshafen (DE); Iori Doi, Amagasaki (JP); Thomas Weitz, Ludwigshafen (DE); Szehui Chua, Singapore (SG); Michael Eustachi, Ludwigshafen (DE)

(73) Assignee: Clap Co., Ltd., Seoul (KR)

( * ) Notice: Subject to any disclaimer, the term of this patent is extended or adjusted under 35 U.S.C. 154(b) by 117 days.

(21) Appl. No.: 16/757,358

(22) PCT Filed: Oct. 11, 2018

(86) PCT No.: PCT/EP2018/077657
§ 371 (c)(1),
(2) Date: Apr. 17, 2020

(87) PCT Pub. No.: WO2019/076709
PCT Pub. Date: Apr. 25, 2019

(65) Prior Publication Data
US 2020/0343458 A1 Oct. 29, 2020

(30) Foreign Application Priority Data
Oct. 19, 2017 (EP) .................................. 17197237

(51) Int. Cl.
H01L 51/00 (2006.01)
H01L 51/05 (2006.01)
C07D 333/50 (2006.01)

(52) U.S. Cl.
CPC ........ *H01L 51/0074* (2013.01); *C07D 333/50* (2013.01); *H01L 51/0068* (2013.01); *H01L 51/0545* (2013.01); *H01L 51/0558* (2013.01)

(58) Field of Classification Search
CPC ............. H01L 51/0074; H01L 51/0068; H01L 51/0558; C07D 333/50
(Continued)

(56) References Cited

U.S. PATENT DOCUMENTS
7,384,814 B2  6/2008 Huitema et al.
2006/0223218 A1 10/2006 Huitema et al.
(Continued)

FOREIGN PATENT DOCUMENTS
CN    105418357 A   3/2016
GB    2 239 248     6/1991
(Continued)

OTHER PUBLICATIONS

Wilson, W., L. Sander, M. Lopez de Alda, M. Lee and S. Wise, "Retention behavior of alkyl-substituted polycyclic aromatic sulfur heterocycles in reversed-phase liquid chromatography", J. Chromatogr. A 1461 (2016), pp. 120-130. (Year: 2016).*
(Continued)

*Primary Examiner* — Joseph R Kosack
*Assistant Examiner* — Sagar Patel
(74) *Attorney, Agent, or Firm* — Morrison & Foerster LLP (57) ABSTRACT

The present invention provides compounds of formulae (1) (2) wherein $R^1$ and $R^2$ are $C_{1-30}$alkyl, $C_{2-3}$O-alkenyl, $C_{2-30}$-alkynyl, $C_{5-7}$-cycloalkyl, $C_{6-14}$-aryl or 5 to 14 membered heteroaryl, wherein $C_{1-30}$-alkyl, $C_{2-3}$O-alkenyl and $C_{2-3}$O-alkynyl can be substituted with one or more substituents selected from the group consisting of halogen, phenyl, O—$C_{1-20}$-alkyl, O—$C_{2-20}$-alkenyl and O—$C_{2-2}$O-alkynyl, and wherein $C_{5-7}$-cycloalkyl, $C_{6-14}$-aryl and 5 to 14 membered heteroaryl can be substituted with one or more substituents selected from the group consisting of halogen, $C_{1-20}$alkyl, $C_{2-2}$O-alkenyl, $C_{2-2}$O-alkynyl, O—$C_{1-20}$-alkyl, O—$C_{2-20}$-alkenyl and O—$C_{2-20}$-alkynyl, $R^a$, $R^b$, $R^c$ and $R^d$ are independently and at each occurrence selected from the group consisting of $C_{1-30}$alkyl, $C_{2-30}$-alkenyl, $C_{2-30}$-alkynyl, $C_{6-14}$-aryl and 5 to 14 membered heteroaryl, wherein $C_{1-30}$-alkyl, $C_{2-3}$o-alkenyl and $C_{2-3}$o-alkynyl can be substituted with one or more substituents selected from the group consisting of halogen, phenyl, O—$C_{1-20}$-alkyl, O—$C_{2-20}$-alkenyl and O—$C_{2-20}$-alkynyl, and wherein $C_{5-7}$-cycloalkyl, $C_{6-14}$-aryl and 5 to 14 membered heteroaryl can be substituted with one or more substituents selected from the group consisting of halogen, $C_{1-20}$alkyl, $C_{2-2}$o-alkenyl, $C_{2-2}$0-alkynyl, O—$C_{1-20}$-alkyl, O—$C_{2-20}$-alkenyl and O—$C_{2-2}$o-alkynyl, n and o are independently 0, 1, 2, 3, 4 or 5, and m and p are independently 0, 1, 2 or 3, and to electronic device comprising the compounds of formulae 1 or 2.

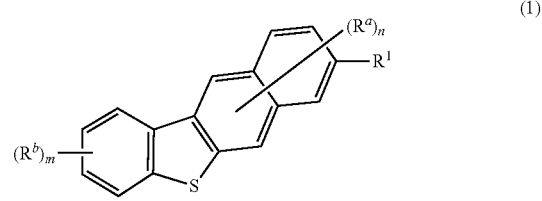

(1)

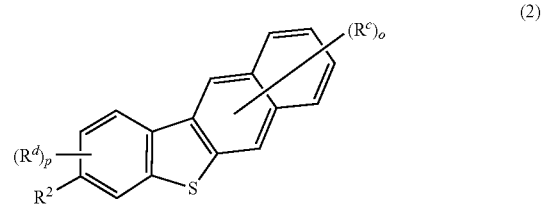

(2)

6 Claims, 3 Drawing Sheets

(58) Field of Classification Search
USPC .............. 549/42; 257/51.047, 51.05, 51.006
See application file for complete search history.

(56) References Cited

U.S. PATENT DOCUMENTS

| | | | |
|---|---|---|---|
| 2011/0121273 A1 | 5/2011 | Jo et al. | |
| 2012/0187379 A1 | 7/2012 | Wu et al. | |
| 2013/0048949 A1 | 2/2013 | Xia et al. | |
| 2014/0004464 A1 | 1/2014 | Christianson et al. | |
| 2014/0296444 A1 | 10/2014 | Chisholm et al. | |
| 2015/0372241 A1* | 12/2015 | Park .................. | C07D 495/04 257/40 |
| 2016/0254466 A1 | 9/2016 | Koizumi et al. | |
| 2017/0141319 A1 | 5/2017 | Noh | |
| 2018/0026214 A1 | 1/2018 | Tian | |
| 2018/0222910 A1 | 8/2018 | Mun et al. | |
| 2020/0343458 A1 | 10/2020 | Nekelson et al. | |
| 2020/0388772 A1 | 12/2020 | Yamato et al. | |
| 2020/0411781 A1 | 12/2020 | Kwon et al. | |
| 2021/0036248 A1 | 2/2021 | Lin et al. | |

FOREIGN PATENT DOCUMENTS

| | | |
|---|---|---|
| JP | H06 313107 | 11/1994 |
| JP | 2009-069381 | 4/2009 |
| JP | 2010-087408 | 4/2010 |
| JP | 2010-100844 | 5/2010 |
| JP | 2011-012147 | 1/2011 |
| JP | 2012169550 A | 9/2012 |
| JP | 2017-143097 | 8/2017 |
| KR | 10-2012-0104067 | 9/2012 |
| KR | 2013-0075982 | 7/2013 |
| KR | 20130075982 A | 7/2013 |
| KR | 10-2013-0135516 | 12/2013 |
| KR | 10-2015-0065184 | 6/2015 |
| WO | WO 2011/060293 | 5/2011 |
| WO | WO 2014/115749 | 7/2014 |
| WO | WO 2017/022983 | 2/2017 |
| WO | WO2017022983 A1 | 2/2017 |
| WO | WO 2018/104367 | 6/2018 |

OTHER PUBLICATIONS

U.S. Appl. No. 17/255,397, filed Dec. 22, 2020, by Kaelblein et al. (Copy not submitted herewith pursuant to the waiver of 37 C.F. R. § 1.98(a)(2)(iii) issued by the Office dated Sep. 21, 2004).

U.S. Appl. No. 17/285,445, filed Apr. 15, 2021, by Kaelblein et al. (Copy not submitted herewith pursuant to the waiver of 37 C.F. R. § 1.98(a)(2)(iii) issued by the Office dated Sep. 21, 2004).

Cai et al., "Exceptional Single-Molecule Transport Properties of Ladder-Type Heteroacene Molecular Wires," J Am Chem Soc (2016) 138(33): 10630-10635.

Cai et al., "Synthesis of Alternating Donor-Acceptor Ladder-Type Molecules and Investigation of Their Multiple Charge-Transfer Pathways," Angew Chem Int Ed Engl. (2018) 57(22):6442-6448.

Database Caplus [Online] Chemical Abstracts Service, Columbus, Ohio, US; Dec. 12, 2008 (Dec. 12, 2008), Nakatsuka, Masakatsu; Fujiyama, Takahiro; Toya, Yoshiyuki: 11 Organic transistors containing thiophene derivatives with high charge mobility, on/off current ratio, and storage stability 11 , XP002789822, retrieved from STN Database accession No. 2008:1483593 abstract.

Kimura et al., "Soluble Organic Semiconductor Precursor With Specific Phase Separation for High-Performance Printed Organic Transistors," Adv Mater. (2015) 27(4): 727-732.

Nielsen et al., "Recent Advances in the Development of Semiconducting DPP-Containing Polymers for Transistor Applications," Adv Mater (2012) DOI: 10.1002/adma.201201795.

Rafiq et al., "Synthesis of Annulated Thiophenes Involving Benzo-DMTHFs/Triflic acid-Mediated Domino Reactions," Chemistry Select (2017) 2:2578-2582.

Smithson et al., "Using unsorted single-wall carbon nanotubes to enhance mobility of diketopyrrolopyrrole-quarterthiophene copolymer in thin-film transistors," Orgnnic Electronics (2014) 15:2639-2646.

Zheng et al., "Roles of Quinoidal Character and Regioregularity in Determining the Optoelectronic and Photovoltaic Properties of Conjugated Copolymers," Macromolecules (2014) 47:18; 6252-6259.

Campaigne et al., "Some methyl substituted benzo[b]naphtho[2,3-d]thiophenes," Jnl Heterocyclic Chem. (1969) (6)6: 885-889.

Mitsui et al., "High-performance Solution-Processable N-shaped Organic Semiconducting Materials With Stabilized Crystal Phase," Adv Mater (2014) 26(26): 4546-4551.

Okamoto et al., "V-shaped Organic Semiconductors With Solution Processability, High Mobility, and High Thermal Durability," Adv Mater (2013) (44):6392-6397.

Pham et al., "Aromatic Homologation by Non-Chelate-Assisted Rh(III)-catalyzed C—H Functionalization of Arenes With Alkynes," Angew Chem Int Ed Engl. (2014) 53(13): 3484-3487.

Pratap et al., "Synthesis of benzo[b]phenanthro[d]thiophenes," Jnl Heterocyclic Chem. (1982) (19)1: 865-869.

* cited by examiner

SUBSTITUTED BENZONAPHTHATHIOPHENE COMPOUNDS FOR ORGANIC ELECTRONICS

CROSS REFERENCE TO RELATED APPLICATIONS

This application is a National Stage application under 35 U.S.C. § 371 of International Application No. PCT/EP2018/077657, filed internationally on Oct. 11, 2018, which claims priority to European Patent Application No. 17197237.5, filed Oct. 19, 2017, the contents of which are incorporated herein by reference in their entirety.

The present invention relates to compounds of formulae 1 and 2, to electronic devices comprising these compounds and to the use of these compounds as semiconducting material.

Organic semiconducting materials can be used in electronic devices such as organic photovoltaic devices (OPVs), organic field-effect transistors (OFETs), organic light emitting diodes (OLEDs), organic photodiodes (OPDs) and organic electrochromic devices (ECDs).

It is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

For application in organic field-effect transistors (OFETs), it is further desirable that the organic semiconducting materials show high charge carrier mobility and a high on/off ratio, and are stable under ambient conditions regarding temperature, oxygen and humidity.

JP 2010-087408 describes an organic transistor having an organic semiconducting layer containing a compound of formula wherein A represents a structure expressed by formula (a) or (b)

(a)

(b)

JP 2012-169550 describes an organic semiconductor material having a sulfur-containing condensed ring-compound. The sulfur-containing condensed ring compound has a condensed ring skeleton with 4 to 10 condensed rings combining m unit A represented by general formula (1)

(1)

(stars indicates a condensation position), and n units B represented by general formula (2)

(2)

(stars indicates a condensation position) so as to satisfy the relations $4 \leq 3$ m+n$\leq$10, m$\geq$1, n$\geq$0. A specific functional group is bonded to each benzene ring configuring a condensed ring skeleton so as to be asymmetric on the condensed ring skeleton.

JP 2012-169550 exemplifies the following compounds

KR 2013-075982 describes an anthracene-based compound represented by formula (1)

wherein A is a functional group represented by formula (1-a)

It was the object of the present invention to provide improved organic semiconducting materials. This object is solved by the compounds of claim 1 and the device of claim 7.

The compounds of the present invention are compounds of formulae wherein
$R^1$ and $R^2$ are $C_{1-30}$ alkyl, $C_{2-30}$-alkenyl, $C_{2-30}$-alkynyl, $C_{5-7}$-cycloalkyl, $C_{6-14}$-aryl or 5 to 14 membered heteroaryl,
  wherein $C_{1-30}$-alkyl, $C_{2-30}$-alkenyl and $C_{2-30}$-alkynyl can be substituted with one or more substituents selected from the group consisting of halogen, phenyl, O—$C_{1-20}$-alkyl, O—$C_{2-20}$-alkenyl and O—$C_{2-20}$-alkynyl, and
  wherein $C_{5-7}$-cycloalkyl, $C_{6-14}$-aryl and 5 to 14 membered heteroaryl can be substituted with one or more substituents selected from the group consisting of halogen, $C_{1-20}$ alkyl, $C_{2-20}$-alkenyl, $C_{2-20}$-alkynyl, O—$C_{1-20}$-alkyl, O—$C_{2-20}$-alkenyl and O—$C_{2-20}$-alkynyl,
$R^a$, $R^b$, $R^c$ and $R^d$ are independently and at each occurrence selected from the group consisting of $C_{1-30}$ alkyl, $C_{2-30}$-alkenyl, $C_{2-30}$-alkynyl, $C_{6-14}$-aryl and 5 to 14 membered heteroaryl,
  wherein $C_{1-30}$-alkyl, $C_{2-30}$-alkenyl and $C_{2-30}$-alkynyl can be substituted with one or more substituents selected from the group consisting of halogen, phenyl, O—$C_{1-20}$-alkyl, O—$C_{2-20}$-alkenyl and O—$C_{2-20}$-alkynyl, and
  wherein $C_{5-7}$-cycloalkyl, $C_{6-14}$-aryl and 5 to 14 membered heteroaryl can be substituted with one or more substituents selected from the group consisting of halogen, $C_{1-20}$ alkyl, $C_{2-20}$-alkenyl, $C_{2-20}$-alkynyl, O—$C_{1-20}$-alkyl, O—$C_{2-20}$-alkenyl and O—$C_{2-20}$-alkynyl,
n and o are independently 0, 1, 2, 3, 4 or 5, and
m and p are independently 0, 1, 2 or 3.

Preferably, $R^1$ and $R^2$ are $C_{1-30}$ alkyl, $C_{6-14}$-aryl or 5 to 14 membered heteroaryl,
  wherein $C_{1-30}$-alkyl can be substituted with one or more substituents selected from the group consisting of halogen, phenyl, O—$C_{1-20}$-alkyl, O—$C_{2-20}$-alkenyl and O—$C_{2-20}$-alkynyl, and
  wherein $C_{6-14}$-aryl and 5 to 14 membered heteroaryl can be substituted with one or more substituents selected from the group consisting of halogen, $C_{1-20}$ alkyl, $C_{2-20}$-alkenyl, $C_{2-20}$-alkynyl, O—$C_{1-20}$-alkyl, O—$C_{2-20}$-alkenyl and O—$C_{2-20}$-alkynyl.

More preferably, $R^1$ and $R^2$ are $C_{1-30}$ alkyl or 5 to 14 membered heteroaryl,
  wherein 5 to 14 membered heteroaryl can be substituted with one or more substituents $C_{1-20}$ alkyl.

Even more preferably, $R^1$ and $R^2$ are $C_{6-14}$ alkyl or wherein $R^3$ is H or $C_{1-20}$ alkyl.

Even more preferably, $R^1$ and $R^2$ are $C_{6-14}$ alkyl.

Most preferably, $R^1$ and $R^2$ are $C_{6-14}$ alkyl, in particular n-hexyl, n-octyl or 2-hexylthiophene.

Preferably, $R^a$, $R^b$, $R^c$ and $R^d$ are independently and at each occurrence $C_{1-30}$ alkyl, $C_{6-14}$-aryl or 5 to 14 membered heteroaryl,
  wherein $C_{1-30}$-alkyl can be substituted with one or more substituents selected from the group consisting of halogen, phenyl, O—$C_{1-20}$-alkyl, O—$C_{2-20}$-alkenyl and O—$C_{2-20}$-alkynyl, and
  wherein $C_{6-14}$-aryl and 5 to 14 membered heteroaryl can be substituted with one or more substituents selected from the group consisting of halogen, $C_{1-20}$ alkyl, $C_{2-20}$-alkenyl, $C_{2-20}$-alkynyl, O—$C_{1-20}$-alkyl, O—$C_{2-20}$-alkenyl and O—$C_{2-20}$-alkynyl.

More preferably, $R^a$, $R^b$, $R^c$ and $R^d$ are independently and at each occurrence $C_{1-30}$ alkyl or 5 to 14 membered heteroaryl,
  wherein 5 to 14 membered heteroaryl can be substituted with one or more substituents $C_{1-20}$ alkyl.

Even more preferably, $R^a$, $R^b$, $R^c$ and $R^d$ are independently and at each occurrence $C_{6-14}$ alkyl or wherein $R^3$ is H or $C_{1-20}$ alkyl.

Even more preferably, $R^a$, $R^b$, $R^c$ and $R^d$ are independently and at each occurrence $C_{6-14}$ alkyl.

Most preferably, $R^a$, $R^b$, $R^c$ and $R^d$ are independently and at each occurrence $C_{6-14}$ alkyl.

Preferably, n and o are independently 0, 1 or 2.

More preferably, n and o are independently 0 or 1.

Most preferably, n and o are 0.

Preferably, m and p are independently 0 or 1.

Most preferably, m and p are 0.

Preferred compounds of the present invention are compounds of formulae (1')

or (2')

wherein

R$^1$ and R$^2$ are C$_{1-30}$ alkyl, C$_{6-14}$-aryl or 5 to 14 membered heteroaryl, wherein C$_{1-30}$-alkyl can be substituted with one or more substituents selected from the group consisting of halogen, phenyl, O—C$_{1-20}$-alkyl, O—C$_{2-20}$-alkenyl and O—C$_{2-20}$-alkynyl, and wherein C$_{6-14}$-aryl and 5 to 14 membered heteroaryl can be substituted with one or more substituents selected from the group consisting of halogen, C$_{1-20}$ alkyl, C$_{2-20}$-alkenyl, C$_{2-20}$-alkynyl, O—C$_{1-20}$-alkyl, O—C$_{2-20}$-alkenyl and O—C$_{2-20}$-alkynyl.

More preferred compounds of the present invention are compounds of formulae (1')

or (2')

wherein

R$^1$ and R$^2$ are C$_{1-30}$ alkyl or 5 to 14 membered heteroaryl, wherein 5 to 14 membered heteroaryl can be substituted with one or more substituents selected from the group consisting of C$_{1-20}$ alkyl.

Even more preferred compounds of the present invention are compounds of formulae (1')

or

(2')

wherein R$^1$ and R$^2$ are C$_{6-14}$ alkyl or

, wherein R$^3$ is H or C$_{1-20}$ alkyl.

Most preferred compounds of the present invention are compounds of formulae

(1')

or

(2')

wherein R$^1$ and R$^2$ are C$_{6-14}$ alkyl.

Particular preferred compounds of the present invention are the compounds of formulae (1a)

and (2a)

$C_{1-6}$-alkyl, $C_{1-20}$-alkyl, $C_{6-14}$-alkyl and $C_{1-30}$-alkyl can be branched or unbranched. Examples of $C_{1-6}$-alkyl are methyl, ethyl, n-propyl, isopropyl, n-butyl, sec-butyl, isobutyl, tert-butyl, n-pentyl, neopentyl, isopentyl, n-(2,2-dimethyl)propyl, n-(1-ethyl)propyl and n-hexyl. Examples of $C_{1-20}$-alkyl are methyl, ethyl, n-propyl, isopropyl, n-butyl, sec-butyl, isobutyl, tert-butyl, n-pentyl, neopentyl, isopentyl, n-(2,2-dimethyl)propyl, n-(1-ethyl)propyl, n-hexyl, n-heptyl, 2-heptyl, n-octyl, 2-octyl, n-(3-methyl)heptyl, n-(1,1,3,3-tetramethyl)butyl, n-(2-ethyl)hexyl, n-nonyl, n-(1,1,3,3-tetramethyl)pentyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl are $C_{1-20}$-alkyl and n-docosyl ($C_{22}$), n-tetracosyl ($C_{24}$), n-hexacosyl ($C_{26}$), n-octacosyl ($C_{28}$) and n-triacontyl ($C_{30}$). Examples of $C_{6-14}$-alkyl are, n-hexyl, n-heptyl, 2-heptyl, n-octyl, 2-octyl, n-(3-methyl)heptyl, n-(1,1,3,3-tetramethyl)butyl, n-(2-ethyl)hexyl, n-nonyl, n-(1,1,3,3-tetramethyl)pentyl, n-decyl, n-undecyl, n-dodecyl, n-undecyl, n-dodecyl, n-tridecyl and n-tetradecyl.

$C_{2-20}$-alkenyl and $C_{2-30}$-alkenyl can be branched or unbranched. Examples of $C_{2-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl, docenyl, linoleyl ($C_{18}$), linolenyl ($C_{18}$), oleyl ($C_{18}$), and arachidonyl ($C_{20}$). Examples of $C_{2-30}$-alkenyl are $C_{2-20}$-alkenyl and erucyl ($C_{22}$).

$C_{2-20}$-alkynyl and $C_{2-30}$-alkynyl can be branched or unbranched. Examples of $C_{2-20}$-alkynyl and $C_{2-30}$-alkynyl are ethynyl, 2-propynyl, 2-butynyl, 3-butynyl, pentynyl, hexynyl, heptynyl, octynyl, nonynyl, decynyl, undecynyl, dodecynyl, undecynyl, dodecynyl, tridecynyl, tetradecynyl, penta-decynyl, hexadecynyl, heptadecynyl, octadecynyl, nonadecynyl and icosynyl ($C_{20}$).

Examples of $C_{6-7}$-cycloalkyl are cyclopentyl, cyclohexyl and cycloheptyl.

Examples of $C_{6-14}$-aryl are phenyl, naphthyl, anthracenyl, phenantrenyl, tetracenyl and chrysenyl.

Examples of 5 to 14 membered heteroaryl are

-continued wherein $R^{100}$ is at each occurrence $C_{1-6}$-alkyl or phenyl.

Halogen can be F, Cl, Br and I.

The compound of formula 1 can be prepared by methods known in the art. For example, the compound of formula 1'

(1')

wherein $R^1$ is $C_{1-30}$ alkyl, $C_{2-30}$-alkenyl, $C_{2-30}$-alkynyl, $C_{5-7}$-cycloalkyl, $C_{6-14}$-aryl or 5 to 14 membered heteroaryl, wherein $C_{1-30}$-alkyl, $C_{2-30}$-alkenyl and $C_{2-30}$-alkynyl can be substituted with one or more substituents selected from the group consisting of halogen, phenyl, O—$C_{1-20}$-alkyl, O—$C_{2-20}$-alkenyl and O—$C_{2-20}$-alkynyl, and wherein $C_{5-7}$-cycloalkyl, $C_{6-14}$-aryl and 5 to 14 membered heteroaryl can be substituted with one or more substituents selected from the group consisting of halogen, $C_{1-20}$ alkyl, $C_{2-20}$-alkenyl, $C_{2-20}$-alkynyl, O—$C_{1-20}$-alkyl, O—$C_{2-20}$-alkenyl and O—$C_{2-20}$-alkynyl, can be prepared from a compound of formula

(3)

by treating the treating the compound of formula 3 with $R^1$MgBr, wherein $R^1$, $R^a$, $R^b$, m and n are as defined for the compound of formula 1, in the presence of a suitable catalyst such as Ni(dppp)Cl$_2$.

The compound of formula 3 can be prepared as described in scheme 1.

Scheme 1.

Compound 10 can be treated with NBS in AcOH/CHCl₃ in order to obtain compound 9. Compound of formula 9 can be treated with n-BuLi in Et₂O at −78° C., followed by p-anisaldehyde in order to obtain compound 8. Compound 8 can be treated with LiAlH₄ and AlCl₃ in Et₂O at 40° C. in order to obtain compound 7. Compound 7 can be treated with n-BuLi in THF at −78° C. followed by DMF in order to obtain compound 6. Compound 6 can be treated with polyphosphoric acid at 50° C. in order to obtain compound 5. Compound 5 can be treated with BBr₃ in DCM, followed by water in order to obtain compound 4. Compound 4 can be treated with pyridine in DCM followed by triflic anhydride at 0° C. in order to obtain compound 3.

The compound of formula 2 can be prepared by methods known in the art. For example, the compound of formula 2' wherein

R² is $C_{1-30}$ alkyl, $C_{2-30}$-alkenyl, $C_{2-30}$-alkynyl, $C_{5-7}$-cycloalkyl, $C_{6-14}$-aryl or 5 to 14 membered heteroaryl, wherein $C_{1-30}$-alkyl, $C_{2-30}$-alkenyl and $C_{2-30}$-alkynyl can be substituted with one or more substituents selected from the group consisting of halogen, phenyl, O—$C_{1-20}$-alkyl, O—$C_{2-20}$-alkenyl and O—$C_{2-20}$-alkynyl, and wherein $C_{5-7}$-cycloalkyl, $C_{6-14}$-aryl and 5 to 14 membered heteroaryl can be substituted with one or more substituents selected from the group consisting of halogen, $C_{1-20}$ alkyl, $C_{2-20}$-alkenyl, $C_{2-20}$-alkynyl, O—$C_{1-20}$-alkyl, O—$C_{2-20}$-alkenyl and O—$C_{2-20}$-alkynyl, can be prepared from a compound of formula (11)

by treating compound 11 with R²MgBr in the presence of a suitable catalyst such a Ni(dppp)Cl₂. Compound 11 can be prepared as described in scheme 2.

Scheme 2.

Compound 14 can be treated with phthalic anhydride in the presence of AlCl₃ in DCM at room temperature in order to obtain compound 13. Compound 13 can be treated with PCl₅ and AlCl₃ in dichlorobenzene at 140° C. in order to obtain compound 12. Compound 12 can be treated with HI and H₃PO₂ in AcOH at 150° C. in order to obtain compound 11.

Also part of the present invention is an electronic device comprising the compounds of formulae 1 or 2. Preferably, the electronic device is an organic field effect transistor (OFET).

Usually, an organic field effect transistor comprises a dielectric layer, a semiconducting layer and a substrate. In addition, an organic field effect transistor usually comprises a gate electrode and source/drain electrodes.

Preferably, the semiconducting layer comprises the compound of formulae 1 or 2. The semiconducting layer can have a thickness of 5 to 500 nm, preferably of 10 to 100 nm, more preferably of 20 to 50 nm.

The dielectric layer comprises a dielectric material. The dielectric material can be silicon dioxide or aluminium oxide, or, an organic polymer such as polystyrene (PS), poly(methylmethacrylate) (PMMA), poly(4-vinylphenol) (PVP), poly(vinyl alcohol) (PVA), benzocyclobutene (BCB), or polyimide (PI). The dielectric layer can have a thickness of 10 to 2000 nm, preferably of 50 to 1000 nm, more preferably of 100 to 800 nm.

The dielectric layer can in addition to the dielectric material comprise a self-assembled mono-layer of organic silane or organic phosphoric acid derivatives. An example of an organic silane derivative is octyltrichlorosilane. An examples of an organic phosphoric acid derivative is octyldecylphosphoric acid. The self-assembled monolayer comprised in the dielectric layer is usually in contact with the semiconducting layer.

The source/drain electrodes can be made from any suitable source/drain material, for example gold (Au) or tantalum (Ta). The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide, gold (Au) and/or tantalum (Ta). The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the design of the organic field effect transistor, the gate electrode, for example highly doped silicon can also function as substrate.

The organic field effect transistor can be prepared by methods known in the art.

For example, a bottom-gate top-contact organic field effect transistor can be prepared as follows: The dielectric material, for example Al₂O₃ or silicon dioxide, can be applied as a layer on a gate electrode such as highly doped silicon wafer, which also functions as substrate, by a suitable deposition method such as atom layer deposition or thermal evaporation. A self-assembled monolayer of an organic phosphoric acid derivative or an organic silane derivative can be applied to the layer of the dielectric material. For example, the organic phosphoric acid derivative or the organic silane derivative can be applied from solution using solution-deposition techniques. The semiconducting layer can be formed by either solution deposition or thermal evaporation in vacuo of a compound of formulae 1 or 2 on the self-assembled monolayer of the organic phosphoric acid derivative or the organic silane derivative. Source/drain electrodes can be formed by deposition of a suitable source/drain material, for example tantalum (Ta) and/or gold (Au), on the semiconducting layer through a shadow masks. The channel width (W) is typically 500 µm and the channel length (L) is typically 1000 µm.

Also part of the invention is the use of the compounds of formulae 1 or 2 as semiconducting material.

The compounds of formulae 1 and 2 show high charge carrier mobility and high stability, in particular towards oxidation, under ambient conditions with regard to temperature, humidity and oxygen. Furthermore, the compounds of formula 1 and 2 are compatible with liquid processing techniques.

EXAMPLES

Example 1

Preparation of Compound 3

Preparation of Compound 9

To a solution of benzothiophene (10) (10 g, 75 mmol) and AcOH (75 mL) in CHCl$_3$ (75 mL) at 0° C. was added NBS (16.6 g, 93 mmol) portion-wise over a period of 15 mins. The reaction mixture was allowed to stir at room temperature overnight. After 15.5 hours, the reaction mixture was diluted with CHCl$_3$. The organic layer was washed with Na$_2$S$_2$O$_3$ (×1), Na$_2$CO$_3$ (×1), water (×1) and dried over Na$_2$SO$_4$. The crude material was purified through flash column chromatography (100% hexane) to yield compound 9 as pale yellow oil (12.86 g, 81%) after solvent removal. $^1$H NMR (400 MHz, CDCl$_3$) δ7.85 (m, 2H), 7.45 (m, 3H).

Preparation of Compound 8

To a solution of compound 9 (9.6 g, 45 mmol) in anhydrous Et$_2$O (150 mL) at −78° C. was added n-BuLi (21.6 mL, 54 mmol) drop-wise. The reaction mixture was allowed to stir at −78° C. for 2 hours. After 2 hours, p-anisaldehyde (5.5 mL, 45 mmol) was then added drop-wise to the reaction mixture at −78° C. The reaction mixture was allowed to warm to room temperature gradually and stir overnight. After overnight stirring at room temperature, the reaction mixture was quenched with NH$_4$Cl. The organic layer was extracted with Et$_2$O (×3). The organic extract was washed with water (×2), brine (×1) and dried over Na$_2$SO$_4$. The crude compound 8 was obtained as a pale yellow oil and was used for the next step without further purification.

Preparation of Compound 7

To a suspension of LiAlH$_4$ (1.9 g, 50 mmol) and AlCl$_3$ (6.7 g, 50 mmol) in anhydrous Et$_2$O (140 mL) at room temperature was added compound 8 (12.9 g, 48 mmol) in ether (20 mL) drop-wise. The reaction mixture was heated at 40° C. After 1.5 hours, the reaction mixture was cooled to room temperature. The reaction was then cooled to 0° C. by an ice bath and quenched by the addition of water drop-wise. The reaction mixture was then poured into 50% H$_2$SO$_4$ solution.

The organic layer was extracted with Et$_2$O (×3). The organic extract was washed with water (×2), brine (×1) and dried over Na$_2$SO$_4$. The crude material was purified by column chromatography (50:50 DCM/Hexane) to yield compound 7 as white solid (7.77 g, 64%). $^1$H NMR (400 MHz, CD$_2$Cl$_2$) δ7.87 (m, 1H), 7.70 (m, 2H), 7.33 (m, 2H), 7.19 (m, 2H), 6.82 (m, 2H), 4.14 (s, 2H), 3.77 (s, 3H).

Preparation of Compound 6

To a solution of compound 7 (5.8 g, 23 mmol) in THF (31 mL) at −78° C. was added n-BuLi (11.0 mL, 27 mmol) drop-wise. The reaction mixture was allowed to stir at −78° C. for 1 hour. After 1 h, DMF (3.5 mL, 46 mmol) was then added drop-wise to the reaction mixture. The reaction mixture was allowed to warm to room temperature and stir overnight. After 18 hours, the reaction mixture was quenched with NH$_4$Cl. The organic layer was extracted with Et$_2$O (×3). The organic extract was washed with water (×3), brine (×1) and dried over Na$_2$SO$_4$. The crude solid was filtered and washed with hexane followed by MeOH. The crude material was purified by column chromatography (10:90 EA/Hexane) to yield compound 6 as yellow solid (6.44 g, 61%). $^1$H NMR (400 MHz, d$_4$-TCE) δ10.31 (s, 1 H), 7.88 (m, 2H), 7.52 (m, 1H), 7.41 (m, 1H), 7.13 (m, 2H), 6.82 (m, 2H), 4.57 (s, 2H), 3.77 (s, 3H).

Preparation of Compound 5

Polyphosphoric acid (50 g) was weighed into a one-neck round bottom flask using a syringe. Compound 6 (4.0 g, 14 mmol) was then added into the flask in one portion. The reaction mixture was heated at 50° C. After 2 hours, the heating was discontinued. Ice water was poured into the reaction mixture. The organic layer was extracted with EA (×3). The organic extract was washed with water (×2), NaHCO$_3$ (×1) and dried over Na$_2$SO$_4$. The crude material was purified by flash column chromatography (50:50 DCM/Hexane) to yield compound 5 as a pale yellow solid (0.67 g, 18%). $^1$H NMR (400 MHz, d$_4$-TCE) δ8.55 (s, 1 H), 8.25 (m, 2H), 7.95 (m, 1H), 7.85 (m, 1 H), 7.50 (m, 2H), 7.20 (m, 2H), 3.97 (s, 3H).

Preparation of Compound 4

To 4-methoxy-naphtha[2,3-b]benzo[d]thiophene (0.6 g, 2 mmol) in anhydrous DCM (12 mL) at room temperature was added BBr$_3$ (3.7 mL, 4 mmol) drop-wise slowly. The reaction mixture was stirred at room temperature overnight. After 24 hours, the reaction mixture was diluted with water and NaHCO$_3$. The organic layer was extracted with EA (×3). The organic extract was washed with water (×2), brine (×1) and dried over Na$_2$SO$_4$. The crude material (0.57 g, 95%) as a pale yellow solid was used for the next step without further purification. $^1$H NMR (400 MHz, d$_4$-TCE) δ8.56 (s, 1 H), 8.23 (m, 1H), 8.14 (m, 1H), 7.98 (m, 1H), 7.83 (m, 1H), 7.50 (m, 2H), 7.20 (s, 1H), 7.17 (s, 1H).

Preparation of Compound 3

To compound 4 (0.57 g, 2 mmol) in anhydrous DCM (23 mL) was added pyridine (0.38 mL, 5 mmol) slowly. The reaction mixture was cooled to 0° C. and triflic anhydride (0.47 mL, 3 mmol) was added drop-wise. The reaction mixture was then warmed to room temperature. After 1 hour, the reaction mixture was quenched with 10% HCl. The organic layer was extracted with EA (×3). The organic extract was washed with 10% HCl (×1), water (×2), brine (x1) and dried over Na$_2$SO$_4$. Crude compound 3 was purified with flash column chromatography (20:80 EA/Hexane) to give compound 3 as a pale yellow solid (0.79 g, 96%). $^1$H NMR (400 MHz, d$_4$-TCE) δ8.69 (s, 1 H), 8.37 (s, 1H), 8.31 (d, 1H, J=1.6 Hz), 8.15 (d, 1H, J=9.2 Hz), 7.89 (d, 1H, J=2.0 Hz), 7.83 (s, 1 H), 7.56 (m, 2H), 7.42 (d, 1H, J=9.2 Hz).

Example 2

Preparation of Compound 1a

To compound 3 (0.8 g, 2 mmol) and Ni(dppp)Cl$_2$ (55 mg, 0.10 mmol) in anhydrous THF (4 mL) at room temperature was added C$_8$H$_{17}$MgBr (2.4 mL, 2 mmol) drop-wise. The reaction mixture was heated at 80° C. After 5.5 h, the reaction mixture was quenched with water. The organic layer was extracted with DCM (×3) and dried over Na$_2$SO$_4$. The crude material was purified with flash column chromatography (10:90 DCM/Hexane) to give compound 1a as a white solid (0.35 g, 49%). M.p. 120° C.; $^1$H NMR (400 MHz, d$_4$-TCE) δ8.59 (s, 1 H), 8.26 (m, 2H), 7.98 (m, 1H), 7.84 (m, 1H), 7.69 (s, 1H), 7.50 (m, 2H), 7.40 (m, 1H), 2.81 (m, 2H), 1.76-1.67 (m, 6H), 1.41-1.1.30 (m, 6H), 0.90 (m, 3H).

Example 3

Preparation of Compound 11

Preparation of Compound 13

To a suspension of AlCl$_3$ (9.4 g, 70 mmol) in anhydrous DCM (213 mL) at room temperature was added phthalic anhydride (3.5 g, 24 mmol) in one portion. The suspension was allowed to stir at room temperature for 15 mins. The suspension was then cooled to 0° C. and compound 14 (5.0 g, 24 mmol) in DCM (10 mL) was added drop-wise. The reaction mixture was stirred overnight at room temperature. After 15.5 h, the reaction mixture was poured into ice water and acidified with 10% HCl. The suspension was filtered through celite, washing with DCM. The filtrate was concentrated to obtain the precipitate. The crude solid was then recrystallized with toluene to yield compound 13 as a pale yellow solid (4.2 g, 50%). $^1$H NMR (400 MHz, DMSO) δ8.39 (s, 1 H), 7.99 (m, 1H), 7.89 (m, 1H), 7.75 (m, 2H), 7.57 (m, 1H), 7.23 (m, 1H), 7.15 (m, 1H).

Preparation of Compound 12

To compound 13 (4.2 g, 12 mmol) and PCl$_5$ (4.9 g, 23 mmol) in anhydrous 1,2-dichlorobenzene (117 mL) at room temperature was added AlCl$_3$ (3.1 g, 23 mmol) portion-wise. The reaction mixture was heated at 140° C. After 4.5 hours, the heating was discontinued. The reaction mixture was diluted with DCM and poured onto ice. The mixture was filtered through celite, washing with DCM. The filtered mixture was extracted with DCM (×3) and dried over Na$_2$SO$_4$. The crude mixture was then distilled to remove excess 1,2-dichlorobenzene and later purified by flash column chromatography (80:20 DCM/Hexane) to yield compound 12 as a dark green solid (3.11 g, 78%). $^1$H NMR (400 MHz, CDCl$_3$) δ8.78 (m, 1 H), 8.26 (m, 2H), 8.12 (s, 1H), 7.77 (m, 2H), 7.72 (m, 1H).

Preparation of Compound 11

To compound 12 (2.5 g, 7 mmol) in AcOH (72 mL) at room temperature was added HI (7.1 mL, 54 mmol) and H$_3$PO$_2$ (1.6 mL, 14 mmol) drop-wise. The reaction mixture was heated at 150° C. overnight. After 26 hours, heating was discontinued and the reaction mixture was poured onto 1% NaHSO$_3$ solution (500 mL). The precipitate was collected by vacuum filtration. The crude solid was purified by column chromatography (40:60 DCM/Hexane) to give compound 11 as a pale yellow solid (0.62 g, 27%). $^1$H NMR (400 MHz, d$_4$-TCE) δ8.62 (s, 1 H), 8.31 (s, 1H), 8.15 (d, 1H, J=8.4 Hz), 8.06 (d, 1H, J=7.6 Hz), 8.00 (s, 1H), 7.93 (d, 1H, J=7.6 Hz), 7.64 (d, 1H, J=8.4 Hz), 7.57 (m, 2H).

Example 4

Preparation of Compound 2a

To compound 11 (375 mg, 1.2 mmol) and Ni(dppp)Cl$_2$ (32.4 mg, 0.1 mmol) in anhydrous THF (2.4 mL) at room temperature was added C$_6$H$_{13}$MgBr (1.8 mL, 1.8 mmol) drop-wise. The reaction mixture was heated at 80° C. overnight. After 18 h, the reaction mixture was quenched with water. The organic layer was extracted with DCM (×3). The organic extract was washed with brine (×1) and dried over Na$_2$SO$_4$. The crude material was purified by column chromatography (10:90 DCM/Hexane) to give compound 2a as a white solid (0.28 g, 73%). M.p. 100° C.; $^1$H NMR (400 MHz, d$_4$-TCE) δ8.58 (s, 1 H), 8.29 (s, 1H), 8.18 (s, 1H), 8.05 (m, 1H), 7.91 (m, 1H), 7.66 (s, 1H), 7.53 (m, 2H), 7.33 (m, 1H), 2.77 (m, 2H), 1.73-1.60 (m, 4H), 1.41-1.1.27 (m, 4H), 0.90 (m, 3H).

Example 5

Preparation of compound 2b

Preparation of compound 20

To 2-hexylthiophene (1.00 g, 6.0 mmol) in anhydrous THF (14 mL) at −78° C. was added n-BuLi (4.1 mL, 1.6M in hexane) drop-wise. The reaction mixture was gradually warmed to room temperature for 1.5 hour. After 1.5 hour, the reaction mixture was cooled down to −78° C. and Me$_3$SnCl (1.53 g, 7.7 mmol) in THF (2 mL) was added drop-wise. The reaction mixture was warmed to room temperature and stirred overnight. After 22 hours, the reaction mixture was quenched with NH$_4$Cl. The organic layer was extracted three times with Et$_2$O. The organic extract was washed with two times with water, once with brine and dried over Na$_2$SO$_4$. The crude material was purified by kugelrohr distillation (150° C. @3 mm Hg) to give compound 20 as a pale yellow oil (0.67 g, 34%). $^1$H NMR (400 MHz, CDCl$_3$) δ7.01 (s, 1 H), 6.90 (s, 1 H), 2.86 (m, 2H), 1.68 (m, 2H), 1.36-1.30 (m, 6H), 0.90 (m, 3H), 0.34 (m, 9H).

Preparation of Compound 2b

To compound 11 (0.53 g, 1.7 mmol) and compound 20 (0.67 g, 2 mmol) in a reaction flask was added anhydrous DMF (28 mL) at room temperature. Pd(PPh$_3$)$_4$ (195 mg, 0.17 mmol) was then added to the reaction mixture under N$_2$ atmosphere in one portion. The reaction mixture was heated at 90° C. for 18 h. The reaction mixture was quenched with water. The organic layer was extracted with DCM (×2). The organic extract was washed with brine and dried over Na$_2$SO$_4$. The crude material was purified by column chromatography (5:95 DCM/Hexane) to give compound 2b as a white solid (0.23 g, 33%). $^1$H NMR (400 MHz, d$_4$-TCE) δ8.48 (s, 1 H), 8.26 (s, 1H), 8.15 (s, 1H), 8.05 (m, 1H), 7.96 (m, 1H), 7.66 (s, 1H), 7.55 (m, 2H), 7.36 (m, 1H), 7.22 (m, 1 H), 6.78 (m, 1 H), 2.88 (m, 2H), 1.72-1.69 (m, 2H), 1.44-1.30 (m, 6H), 0.90 (m, 3H).

Example 5

Preparation of bottom-gate top-contact organic field effect transistors (OFETs) comprising compounds 1a, 2a, respectively, 2b, as semiconducting material 30 nm Al$_2$O$_3$ coated, highly doped silicon wafers were thoroughly cleaned with 2-propanol and after a short oxygen plasma treatment functionalized with decylphosphonic acid (when compound 1a was used as semiconducting material, respectively octadecylphosphonic acid (when compounds 2a or 2b were used as semiconducting material) from solution in 2-propanol. The highly-doped silicon is used as substrate and gate electrode, the decylphosphonic acid, respectively octadecylphosphonic acid treated Al$_2$O$_3$ acts as the gate dielectric. The organic semiconducting material 1a, 2a, respectively, 2b was thermally evaporated in high vacuum (<10$^{-5}$ mbar) while the substrate was held at 40° C. (when compound 1a was used as semiconducting material), respectively at 30° C. (when compounds 2a or 2b were used as semiconducting material). A 50 nm-thick of Au layer for source and drain electrodes was deposited through a shadow mask to give top contact OFET devices. The channel width (W) was 500 μm and channel length (L) was 100 μm.

The output curves and the transfer curves of the organic field effect transistors were determined in ambient air and in the dark using a B1500 Agilent parameter analyzer.

Figure 1:
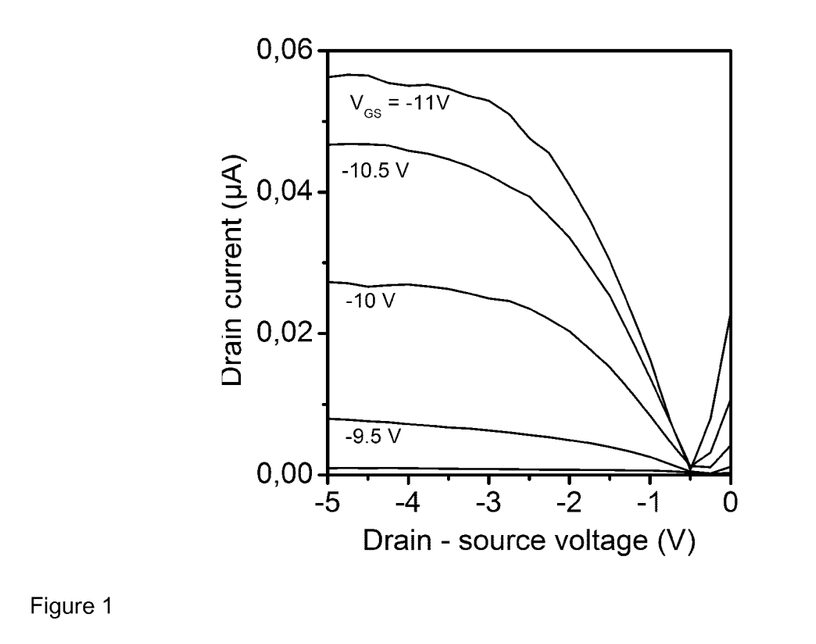
FIG. 1 shows the drain current $I_D$ [A] in relation to the drain-source voltage $V_{DS}$ [V] (output curve) for the bottom-gate top-contact organic field effect transistor comprising compound 1a as semiconducting material at a gate-source voltage $V_{GS}$ of −11 V (first and top curve), −10.5 V (second curve), −10 V (third curve) and −9.5 V (fourth and bottom curve).

FIG. 1 shows the drain current I$_D$ [A] in relation to the drain-source voltage V$_{DS}$ [V] (output curve) for the bottom-gate top-contact organic field effect transistor comprising compound 1a as semiconducting material at a gate-source voltage V$_{GS}$ of −11 V (first and top curve), −10.5 V (second curve), −10 V (third curve) and −9.5 V (fourth and bottom curve).

Figure 2:
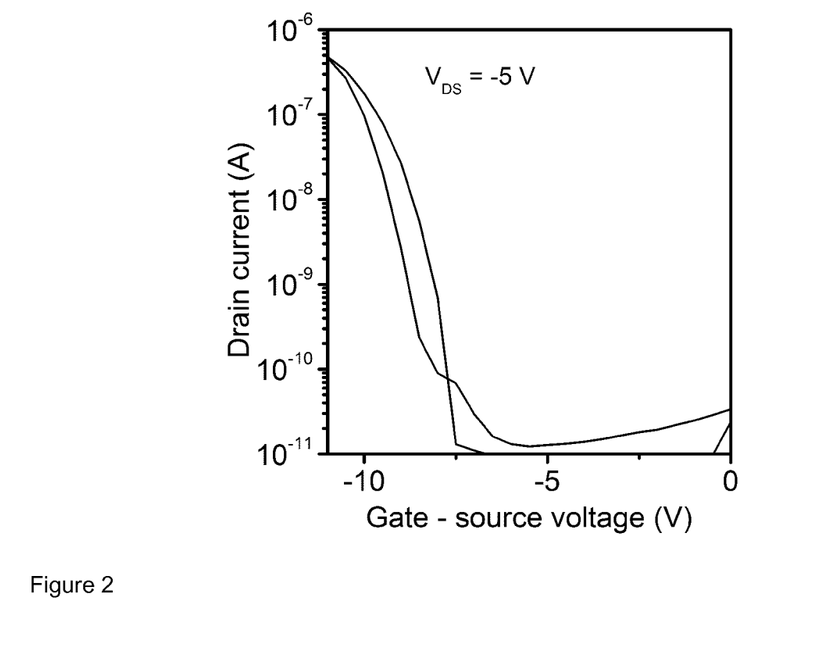
FIG. 2 shows the drain current $I_D$ [A] in relation to the gate-source voltage $V_{GS}$ [V] (transfer curve) for the bottom-gate top-contact organic field effect transistor comprising compound 1a as semiconducting material at a drain-source voltage $V_{DS}$ of −5 V.

FIG. 2 shows the drain current I$_D$ [A] in relation to the gate-source voltage V$_{GS}$ [V] (transfer curve) for the bottom-gate top-contact organic field effect transistor comprising compound 1a as semiconducting material at a drain-source voltage V$_{DS}$ of −5 V.

Figure 3:
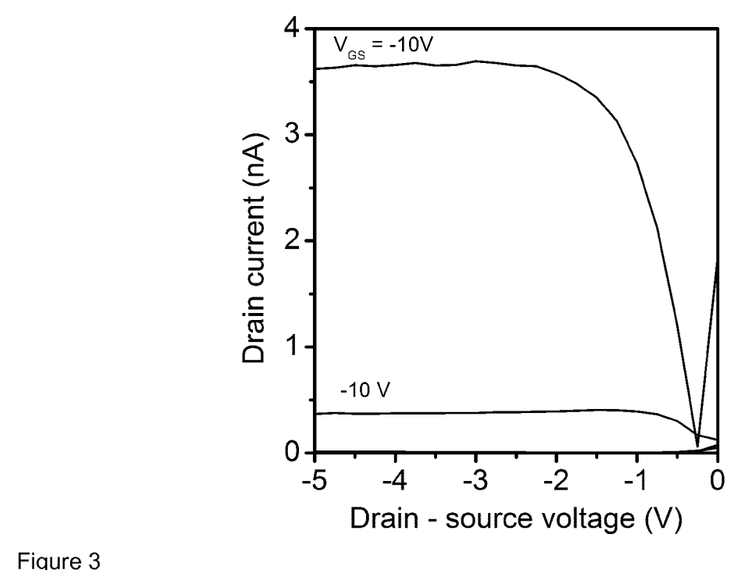
FIG. 3 shows the drain current $I_D$ [A] in relation to the drain-source voltage $V_{DS}$ [V] (output curve) for the bottom-gate, top-contact organic field effect transistor comprising compound 2a as semiconducting material at a gate-source voltage $V_{GS}$ of −10 V (first and top curve).

FIG. 3 shows the drain current I$_D$ [A] in relation to the drain-source voltage V$_{DS}$ [V] (output curve) for the bottom-gate, top-contact organic field effect transistor comprising compound 2a as semiconducting material at a gate-source voltage V$_{GS}$ of −10 V (first and top curve).

Figure 4:
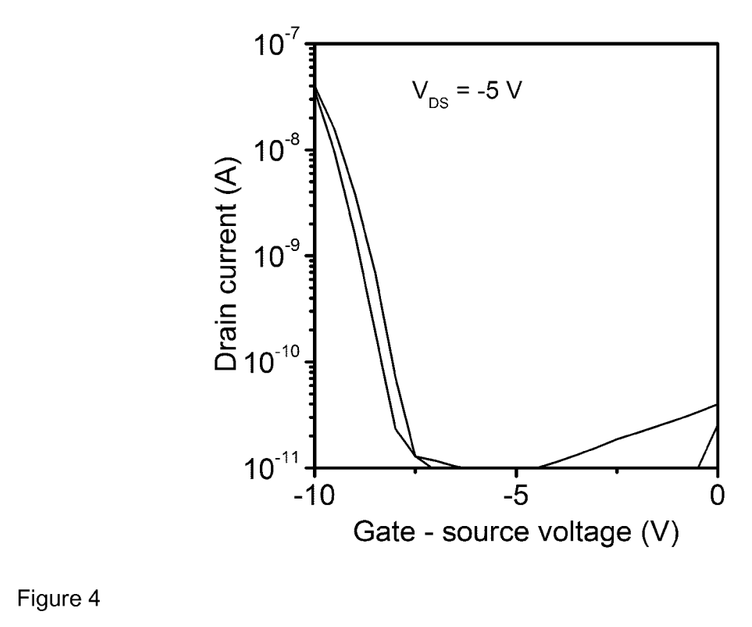
FIG. 4 shows the drain current $I_D$ [A] in relation to the gate-source voltage $V_{GS}$ [V] (transfer curve) for the bottom-gate top-contact organic field effect transistor comprising compound 2a as semiconducting material at a drain-source voltage $V_{DS}$ of −5 V.

FIG. 4 shows the drain current I$_D$ [A] in relation to the gate-source voltage V$_{GS}$ [V] (transfer curve) for the bottom-gate top-contact organic field effect transistor comprising compound 2a as semiconducting material at a drain-source voltage V$_{DS}$ of −5 V.

Figure 5:
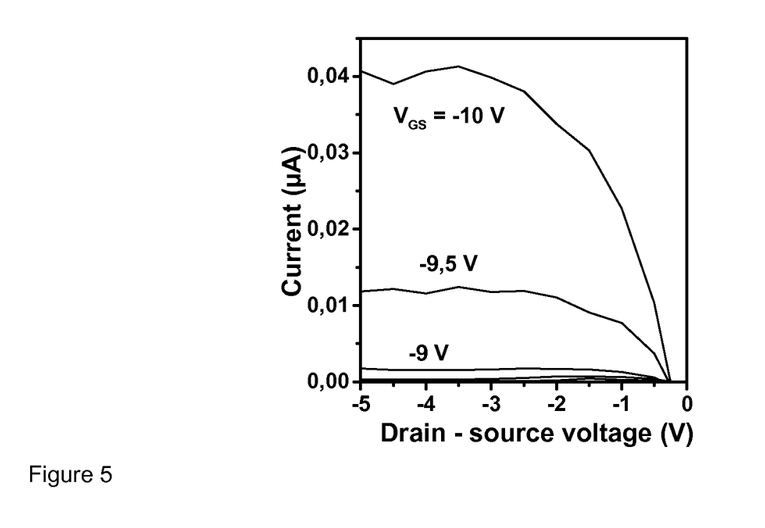
FIG. 5 shows the drain current $I_D$ [A] in relation to the drain-source voltage $V_{DS}$ [V] (output curve) for the bottom-gate, top-contact organic field effect transistor comprising compound 2b as semiconducting material at a gate-source voltage VGS of −10 V (first and top curve), −9.5 V (second curve) and −9 V (third and bottom curve).

FIG. 5 shows the drain current I$_D$ [A] in relation to the drain-source voltage V$_{DS}$ [V] (output curve) for the bottom-gate, top-contact organic field effect transistor comprising compound 2b as semiconducting material at a gate-source voltage V$_{GS}$ of −10 V (first and top curve), −9.5 V (second curve) and −9 V (third and bottom curve).

Figure 6:
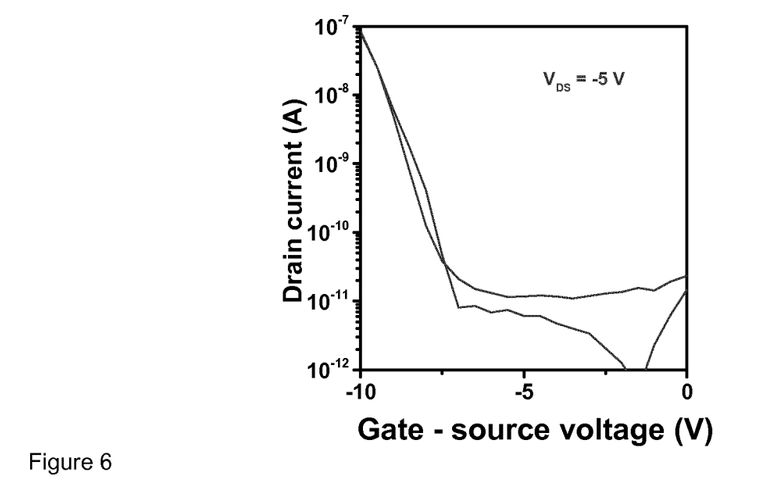
FIG. 6 shows the drain current $I_D$ [A] in relation to the gate-source voltage $V_{GS}$ [V] (transfer curve) for the bottom-gate top-contact organic field effect transistor comprising compound 2b as semiconducting material at a drain-source voltage VDS of −5 V.

FIG. 6 shows the drain current I$_D$ [A] in relation to the gate-source voltage V$_{GS}$ [V] (transfer curve) for the bottom-gate top-contact organic field effect transistor comprising compound 2b as semiconducting material at a drain-source voltage V$_{DS}$ of −5 V.

The compounds 1a, 2a and 2b show typical behavior of p-type semiconducting materials.

The charge-carrier mobility (μ) was extracted in the saturation regime from the slope of (I$_D$)$^{1/2}$ versus V$_{GS}$ using the equation $$\mu = \{2L/(W \times C_i)\} \times (dI_D^{1/2}/dV_{GS}^{1/2})^2$$

wherein L denotes the channel length; W denotes the channel width; C$_i$ denotes the capacitance per unit area of the gate dielectric; I$_D$ denotes the drain source current and V$_{GS}$ denotes the gate-source voltage.

The threshold voltage (V$_{th}$) was extracted from the intersection of the linear extrapolation of the I$_D$$^{1/2}$ versus V$_{GS}$ plot with the V$_{GS}$ axis.

The average values of the threshold voltage V$_{th}$, the charge carrier mobility μ, and the I$_{ON}$/I$_{OFF}$ ratios are given in table 1.

TABLE 1

| Compound | V$_{th}$ [V] | μ [cm$^2$/Vs] | I$_{on/off}$ |
|---|---|---|---|
| 1a | −8.5 | 0.39 | 8 × 10$^5$ |
| 2a | −8.6 | 0.01 | 6 × 10$^4$ |
| 2b | −8.7 | 0.22 | 2 × 10$^5$ |

Comparative Example 1

Preparation of Compound 15

Preparation of Compound 18

To a suspension of AlCl$_3$ (3.75 g, 28 mmol) in anhydrous DCM (108 mL) at room temperature was added phthalic anhydride (2.09 g, 14 mmol) in one portion. The suspension was allowed to stir at room temperature for 15 mins. The suspension was then cooled to 0° C. and 5-bromo-benzo[b]thiophene (3.0 g, 14 mmol) in DCM (10 mL) was added dropwise. The reaction mixture was stirred overnight for 4 h at room temperature. The reaction mixture was poured into ice water and quenched with 10% aqueous sodium carbonate. The organic phase was washed twice with water, treated with 10% solution of hydrochloric acid, washed twice with water, brine and dried over magnesium sulfate. The orange solid obtained after solvent evaporation was recrystallized from toluene to yield compound 18 as a yellow solid (1.83 g, 36%). $^1$H NMR (400 MHz, CDCl$_3$) δ7.92 (s, 2H), 7.67 (d, 2H), 7.45 (m, 4H).

Preparation of Compound 17

To 2-(5-bromobenzo[b]thiophene-2-carbonyl)benzoic acid (1.33 g, 3.7 mmol) and PCl$_5$ (1.53 g, 7.4 mmol) in 1,2-dichlorobenzene (37 mL) at room temperature was added AlCl$_3$ (1.0 g, 7.4 mmol) portion-wise. The reaction mixture was then heated at 140° C. After 4.5 hours, the heating was stopped. The reaction mixture was diluted with DCM and poured onto ice. The mixture was filtered through celite, washing with DCM. The filtered mixture was extracted with DCM (×3) and dried over Na$_2$SO$_4$. The crude mixture was then distilled to remove excess 1,2-dichlorobenzene and later purified by flash column chromatography (50:50 DCM/Hexane) to yield compound 17 as a yellow solid (1.09 g, 86%). $^1$H NMR (400 MHz, CDCl$_3$) δ9.12 (d, 1 H), 8.30-8.24 (m, 2H), 7.85-7.69 (m, 3H), 7.67 (d, 1H).

Preparation of Compound 16

To 2-bromo-6,11-dione-naphta[2,3-b]benzo[d]thiophene (0.47 g, 1.4 mmol) in AcOH (14 mL) at room temperature was added HI (1.4 mL, 10 mmol) and H$_3$PO$_2$ (0.3 mL, 2.7 mmol) dropwise. The reaction mixture was heated at 150° C. overnight. After 24 hours, heating was discontinued and the reaction mixture was poured onto 1% NaHSO$_3$ solution (500 mL). The precipitate was collected by vacuum filtration. The crude solid was purified by column chromatography (17:83 DCM/Hexane) to give compound 16 as a white solid (0.17 g, 37%). $^1$H NMR (400 MHz, CDCl$_3$) δ8.60 (s, 1 H), 8.40 (d, 1H), 8.29 (s, 1H), 8.03 (d, 1H), 7.92 (d, 1H), 7.69 (d, 1H), 7.60-7.51 (m, 3H).

Preparation of Compound 15

To 2-bromo-naphtha[2,3-b]benzo[d]thiophene (0.17 g, 0.5 mmol) and Ni(dppp)Cl$_2$ (15 mg, 0.03 mmol) in anhydrous THF (3 mL) at room temperature was added C$_6$H$_{13}$MgBr (1.0 mL, 0.8 mmol) dropwise. The reaction mixture was stirred at room temperature overnight. The reaction mixture was quenched with water. The organic layer was extracted with ethyl acetate (×2). The organic extract was washed with water (×1) and then brine (×1) and dried over Na$_2$SO$_4$. The crude material was purified by column chromatography (10:90 DCM/Hexane) to give compound 15 as a yellow oil (0.04 g, 23%). 8.61 (s, 1H), 8.26 (s, 1H), 8.08 (s, 1H), 8.03 (d, 1H), 7.81 (d, 1H), 7.72 (d, 1H), 7.50 (m, 2H), 7.32 (d, 1H), 2.80 (m, 2H), 1.73 (m, 2H), 1.35 (m, 6H), 0.90 (m, 3H).

It was not possible to fabricate an organic field effect transistor using compound 15 as semiconducting material, because compound 15 is liquid at room temperature and no solid film could be obtained.

The invention claimed is:

1. Compounds of formulae (1')

or (2')

wherein R$^1$ and R$^2$ are C$_{6-14}$ alkyl or wherein R$^3$ is H or C$_{1-20}$ alkyl.

2. Compounds of claim 1, wherein R$^1$ and R$^2$ are C$_{6-14}$ alkyl.

3. Compounds of claim 2 which are of formulae (1a)

and (2a)

4. An electronic device comprising the compounds of claim 1.

5. The electronic device of claim 4, wherein the electronic device is an organic field effect transistor (OFET).

6. The method of forming a semiconducting layer comprising performing a solution deposition or thermal evaporation in vacuo of the compounds of claim 1.

* * * * *